United States Patent [19]

Friedlander

[11] 4,236,328

[45] Dec. 2, 1980

[54] SHOE WITH ADJUSTABLE ORTHOPEDIC APPLIANCE

[76] Inventor: Bruce W. Friedlander, 129 Joralemon St., Brooklyn, N.Y. 11201

[21] Appl. No.: 94,964

[22] Filed: Nov. 16, 1979

[51] Int. Cl.³ .................... A43B 23/28; A43B 5/04; A61F 13/06
[52] U.S. Cl. ................................ 36/58.5; 36/119; 128/166
[58] Field of Search ............. 36/58.5, 119; 128/166, 128/166.5, 611

[56] References Cited

U.S. PATENT DOCUMENTS

| 2,749,629 | 6/1956 | Scala | 36/58.5 |
| 3,522,668 | 8/1970 | Fesl | 36/119 |
| 4,085,746 | 4/1978 | Castiglia | 128/166 |

Primary Examiner—Patrick D. Lawson
Attorney, Agent, or Firm—Kirschstein, Kirschstein, Ottinger & Cobrin

[57] ABSTRACT

A shoe with a built-in appliance essentially consisting of two length-adjustable bands, each starting from approximately the same point, namely, the mid-point of a shoe sole, nearer to the outer edge than to the inner edge. Each band, which may be made up of more than one strip, extends upwardly to an anchor in the upper part of the shoe. The upper anchor can be on the outside of the shoe, in which event, the bands will pass through slots in the lower part of the shoe upper. The bands diverge from each other in an upward direction and thereby form what, in effect, are a pair of divergent slings.

4 Claims, 7 Drawing Figures

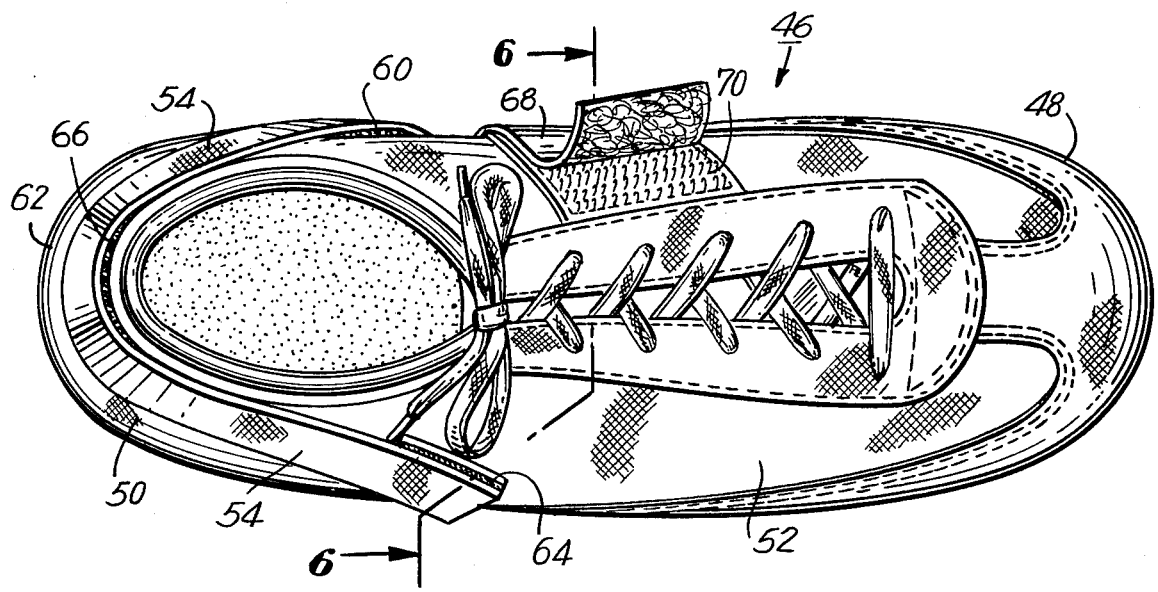
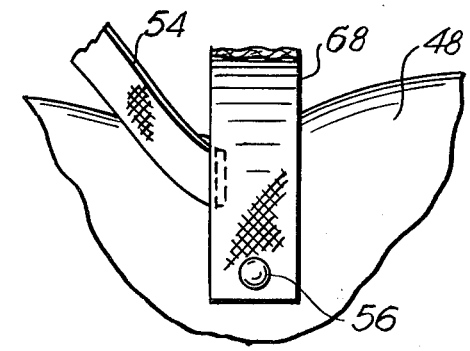
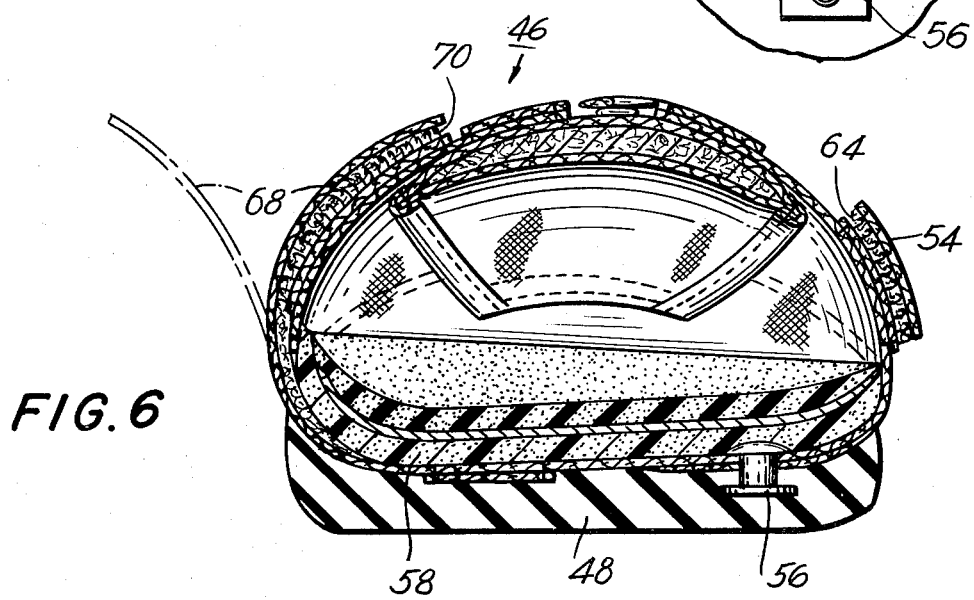

SHOE WITH ADJUSTABLE ORTHOPEDIC APPLIANCE

BACKGROUND OF THE INVENTION

1. Field of the Invention

An orthopedic shoe.

2. Description of the Prior Art

Orthopedic devices either can be purchased in stores or they can be made to order. The ones purchased in stores, since they are intended to fit a wide range of feet, are not hand-tailored to any particular person and therefore are not of much use. The ones that are hand-tailored to persons are of two types; one is an orthopedic appliance which is intended to be slipped into a shoe and hence can be used on a series of shoes of the same person; the other device is built into a shoe and forms a permanent part thereof, not being transferrable from one shoe to another.

The way these orthopedic devices of the hand fitted type have been made heretofore is to have a person place his foot on a moldable substance and leave an impression. The impression usually is taken while the foot is in its horizontal position and not carrying any weight except enough weight to form the impression. Obviously, there are variants on this method of making the impression. In any event, from this impression the orthopedist forms a mold and places it in the shoe or makes an appliance of it for insertion in the shoe.

There are several drawbacks to this method of approach. The first, and probably the foremost, is the high cost. They range from $75.00 and up, exclusive of the price of the shoe. The second is that the orthopedic appliance is not adjustable, so that if a mistake is made, either the customer suffers with it or he has to go back and waste time and possibly pay more money for a re-fitting, i.e. change in the shape of the appliance. Another problem with the appliances is that, as a rule, they are quite rigid and they have no give, so that they tend to be uncomfortable and form callouses on the soles of the feet. A further problem is that as the foot moves, during walking for example, the appliance does not experience an exactly corresponding movement. Hence, the skin is chafed. Therefore, with a new appliance, and sometimes even with an old appliance, painful soreness of the skin or blistering results. Another problem arises when the weight of the person changes to any appreciable extent. A change in weight means a change in the load that is supported by the skeletal structure of the foot and a change in the requisite shape of the orthopedic appliance needed to afford proper support to the foot. An appliance which is a permanent one cannot be changed to accommodate a change in weight. Another problem is where the person with the fitted appliance engages in strenuous activity, for example plays tennis or runs or plays handball. An appliance which is ideally fitted for everyday use in walking will not be properly configured for these more strenuous activities. A further factor is that an insertable appliance may shift. Of course, this is not true of a built-in appliance.

The prior art in general is directed to the provision of bands which are anchored at the mid-point of the insole of a shoe and extend upwardly and, in some instances, through the material of the upper, to an upper anchor at an upper portion of the upper. Usually there is but a single band, with no disclosure of a pair of diverging bands to form a pair of diverging slings, one of which lifts upwardly and rearwardly and the other of which lifts upwardly and forwardly. A single band is contemplated in U.S. Pat. Nos. 1,137,807; 1,649,173; 2,068,251; 2,116,445; 2,149,664; 2,182,843; 3,522,668 and 4,030,215. The U.S. Pat. No. 1,930,188 discloses a pair of bands; one slants upwardly and rearwardly over the tarsal area and the other is at the ball of the foot. This patent does not encompass an arrangement of a mid-tarsal strip with a forward and upward slope.

SUMMARY OF THE INVENTION

1. Purposes of the Invention

It is an object of the present invention to provide an improved orthopedic shoe.

Another object is to provide an improved shoe with an adjustable orthopedic appliance.

A further object is to provide an orthopedic shoe which avoids the various drawbacks of prior art orthopedic appliances.

An additional object is to provide a shoe with an orthopedic appliance which can be inexpensively made in mass-production facilities using unskilled labor.

Still another object is to provide a readily adjustable orthopedic appliance for a shoe, which can be adjusted by the user himself to not only fit his foot but also to make any necessary adjustments as to changes in weight and to changes in nature of activity.

Still a further object is to provide an orthopedic shoe with a pair of adjustable slings which support the instep arch.

An object is to provide an orthopedic shoe with salient advantages over orthotics, e.g. more stabilization with less movement of the foot in the shoe, leading to less blisters due to that movement, lower cost, and immediate adjustability.

An object is to provide an orthodpedic shoe with a front band and a rear band; the front band urging the instep bones upwardly at the midtarsal area, the rear band urging the instep bones rearwardly and upwardly at the tarsal area.

An object is to provide an orthopedic shoe which stabilizes the midtarsal joint by locking the bones of the joint in place and preventing excessive pronation.

An object is to provide a shoe with adjustable orthopedic appliance which, when adjusted properly by the user, will secure the foot in the shoe and prevent or limit movement of the foot in the shoe, thereby reducing shearing forces between the skin and surfaces of the shoe so as to reduce the formation of blisters, corns and callouses.

An object is to provide an orthopedic shoe which, when properly adjusted, supports the longitudinal axis of the foot and thereby reduces arch strain by distributing the weight.

An object is to provide an orthopedic shoe having a structure so that anybody with a foot defect can buy a pair of shoes having the new structure integrally in it, and then can adjust the shoe to fit his individual foot, so that shoes no longer have to be carried with various orthopedic devices, i.e. one shoe will do for all people with a given size of foot.

An object is to provide low cost orthopedic shoe which can be adjusted to accommodate a large number of different deformities.

An object is to provide an orthopedic shoe which stabilizes the mid-tarsal joint, locks the joint and prevents excessive pronation.

An object is to provide a shoe with orthopedic appliance which secures the foot in the shoe and prevents or limits movement of the foot in the shoe, thereby reducing shearing forces thus reducing formation of blisters, corns and callouses.

An object is to provide a shoe with an orthopedic appliance which supports the longitudinal arch in pez planus to reduce arch strain, and redistributes the weight in pez cavus, and supports planter Fascia, thus lessening the chances of heel spurs and supplementing the function of the ligaments, tendons and muscles.

An object is to provide a shoe with orthopedic appliance which is adjustable to all feet of a given size and having a pair of adjustable built-in functional orthotics, and which may be adusted to compensate for forefoot varus deformity as well as non-pathologic forefoot varus, and as well as rear foot varus foot structure.

An object is to provide an orthopedic shoe with wide application and usage, e.g. to running shoes, to orthopedic shoes for all types of foot deformities and malfunctions, to children's pediatric corrective shoes, etc.

An object is to provide an orthopedic shoe improvement that can be used in a running shoe, a sneaker, an ordinary oxford shoe, an everday dress shoe, a ballet shoe, a child's orthopedic shoe, a leather shoe, a canvas shoe, a work shoe, a dance shoe, and virtually any type of men's, women's or children's shoe.

These and other objects and advantages of the present invention will become evident from the description which follows.

2. Brief Description of the Invention

The orthopedic shoe of the present invention avoids the aforementioned drawbacks of prior art appliances, and creates a new appliance which, although a part of the shoe, can be inexpensively made and is a structure which permits the orthopedic shoe to be readily adjustable by the user himself, to not only fit his foot but also to make any necessary adjustments as to changes in weight and to changes in the nature of activity.

Pursuant to the present invention, the manufacturer starts off with an ordinary shoe. It preferably is an Oxford, that is, a low shoe, the upper edge of which is below the ankle. In this shoe is placed two flexible, pliant, non-resilient bands. A slight degree of resilience in the bands is not harmful, but the preferred form has non-resilient bands.

One end of each band is anchored inside the shoe, for example to the insole. It is anchored to the middle of the insole considered in a front-to-back direction, and may be anchored also at the center of the insole in a side-to-side direction, although it preferably is anchored closer to the outer edge of the insole than to the inner edge of the insole. In this regard, the outer edge of the insole is the edge at the outside of the foot and away from the opposite foot; the inner edge of the insole is the edge closest to the opposite foot.

In addition, the present invention provides a feature that permits the lengths of the bands between the two anchored ends to be infinitely adjusted. What is employed is a Velcro fastener for each band. Each band actually is formed in two halves or portions; one half carries one-half of the Velcro fastener. The user adjusts the length of the band in accordance with his desires and for the proper fit of the shoe, and then connects the two halves to each other Fasteners such as Velcro, and constituting two patches or tapes of different natures, are described in U.S. Pat. Nos. 2,717,437; 3,009,235; 3,076,244; 3,083,737; 3,147,528; 3,154,837 and 4,058,853. The usual Velcro fastener includes two mating patches, linear tapes or the like, one provided with a multiplicity of closely spaced plastic monofilamentary loops in the form of a pile, and the other provided with a plurality of closely spaced monofilamentary plastic hooks. The flexible resilient hooks patch, and the loops or pile patch, are typically composed of a plastic such as nylon, polyvinyl chloride, polyvinyl acetate, polyethylene, polypropylene, especially isotactic polypropylene, etc., although metallic wire could be used, such as copper wire, steel wire, brass wire, aluminum wire, etc.

Returning now to the orthopedic shoe per se, the purpose of the two bands is to form a pair of slings for the user, one end of the sling being supported under and about the center of the instep, and the other ends of the slings being on the upper, one at the ankle and the other at a front portion of the upper. The two slings support the instep arch. The front band urges the instep bones upwardly at the midtarsal and metatarsal area, and the rear band urges the instep bones rearwardly at the tarsal area. This action creates forces essentially similar to those created by a conventional orthopedic device. It stabilizes the midtarsal joint. In effect, it locks the bones of the joint in place and prevents excessive pronation. Furthermore, this new device, when adjusted properly by the user, will secure the foot in the shoe and prevent or limit movement of the foot in the shoe, thereby reducing shearing forces (between the skin and surfaces of the shoe). Accordingly, it reduces the formation of blisters, corns and callouses.

The properly adjusted new device also supports the longitudinal axis of the foot and thereby reduces arch strain. It distributes the weight. An excellent advantage of the new structure is that anybody with a foot defect can buy a pair of shoes having this device in it and then can adjust the shoe to fit his individual foot, so that shoes no longer have to be carried with various orthopedic devices—one shoe will do for all people with a given size of foot.

The device is also effective for users with "normal" feet who indulge in normal activities that stress the foot structures beyond their intended purpose in such activities as athletics. Also, the device can be adjusted to accommodate a large number of different deformities. The device can be used in a running shoe, sneaker, an ordinary shoe; it can be used for children or adults. It is quite apparent that the cost will be very low.

To summarize the basic concept of the invention, what has been done is to supply as part of a mass-produced shoe a pair of adjustable-length slings on the inner side of each shoe extending from the center of the insole upwardly and rearwardly, so that two slings are supplied, one urging the foot upwardly and rearwardly, and the other upwardly and forwardly.

The functioning of the present orthopedic shoe with relation to the different phases of gait motion of the foot will now be described. At heel contact, the tarsal strap section prevents the head of the talus bone from moving medially and downwardly from the top of the calcanius bone, therefore preventing excessive pronation at that phase of the gait cycle. At midstance, as the weight of the foot moves more distally over the midtarsal area, the midtarsal strap section tightens and, since it is connected to the tarsal strap section, puts tension on this tarsal strap section, forcing the rear of the foot laterally, thus supinating the rear foot as the forefoot is pronating. At toe-off there is this arrangement whereby when the foot is at toe-off there are forces on the rear of the foot in the direction of supination and the forefoot is pronating, together causing a rigid or locking arrangement of the bones of the foot, making for stable lever of the foot at toe-off.

With regard to other foot problems and deformities, if the foot is splayed, the new orthopedic shoe configuration will supinate the foot by tightening the inside anchor and the anchor at the back of the foot. If the foot is pigeon-toed or has a high arch or walking by the person entails contact and weight concentration on the outside edge (supinating), the new shoe will pronate the foot by loosening between the inside anchor and the back, and tightening between the back and the outside anchor. Finally, the new configuration holds the heel of the foot in the shoe at toe off.

The invention accordingly consists in the features of construction, combination of elements, and arrangement of parts which will be exemplified in the article of manufacture hereinafter described, and of which the scope of application will be indicated in the appended claims.

BRIEF DESCRIPTION OF THE DRAWINGS

In the accompanying drawings in which are shown several of the various possible embodiments of the invention:

FIG. 5 is a plan view of an alternative embodiment of the present orthopedic shoe; and FIG. 6 is a sectional elevation view taken substantially along the line 6—6 of FIG. 5.

FIG. 6a is a partial detail of the shoe of FIG. 6.

DETAILED DESCRIPTION OF THE PREFERRED EMBODIMENTS

Figure 1:
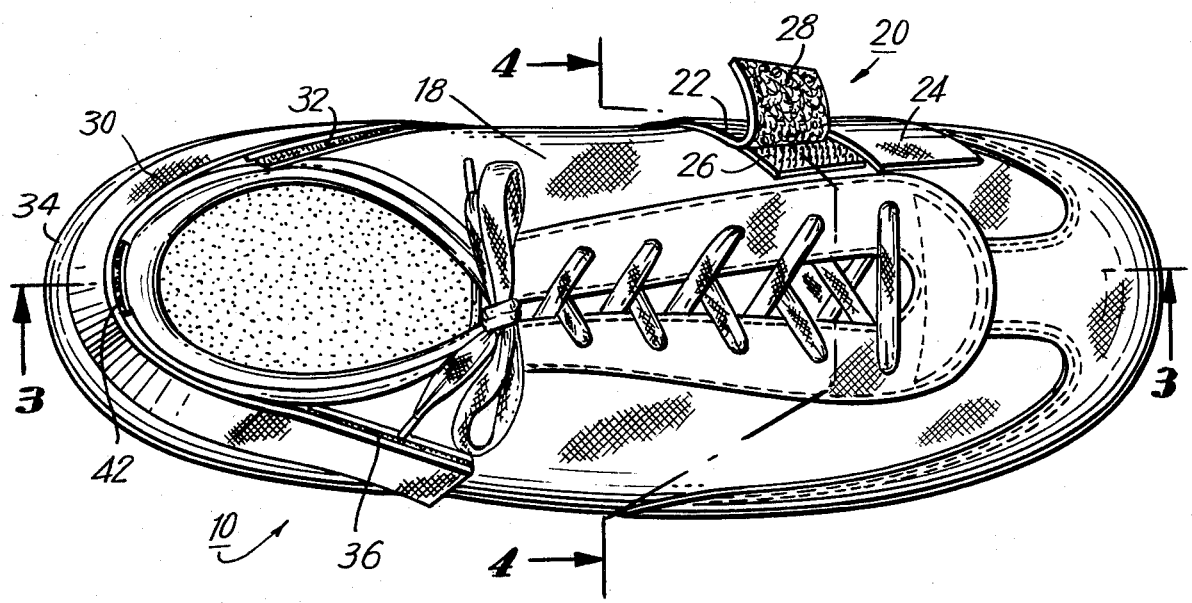
FIG. 1 is a plan view of one embodiment of the present orthopedic shoe with adjustable orthopedic appliance.
Figure 2:
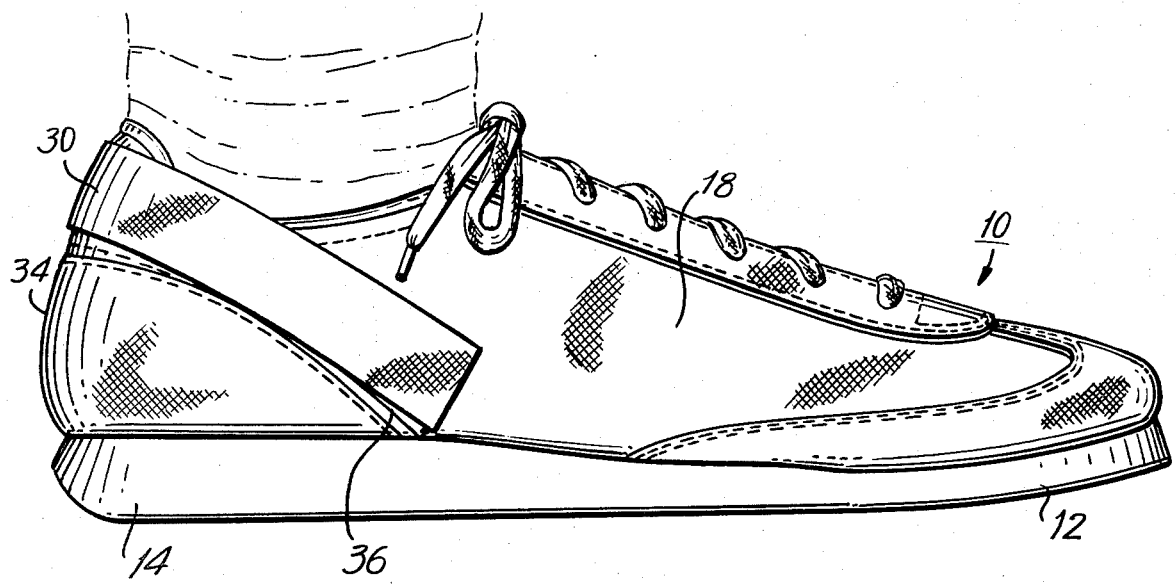
FIG. 2 is a side elevation view of the shoe of FIG. 1.

Referring now to FIGS. 1-4 inclusive, a shoe 10, in this case a shoe for the right foot, has been fitted with one embodiment of the adustable orthopedic appliance of the present invention. The shoe 10 is characterized by the provision of a sole portion 12, a heel portion 14, an insole 16 and an upper portion 18. A first adjustable length sling 20 consists in this case of two generally parallel individual slings 22 and 24, both of which are attached to the same point on the insole 16, and both of which extend forwardly on the outside surface of the inner side of the upper portion 18 of the shoe 10. Thus in essence, the first adjustable length sling 20, on the outside surface of the inner side of the upper portion 18 of the shoe 10, extends from proximately the center of the insole 16 outside of the shoe 10 and external to the upper portion 18 and upwardly and forwardly. The sling 20 (individual slings 22 and 24) extends to a first adjustable anchor 26 on the front part of the upper portion 18 of the shoe 10, the adjustable anchor 26 in this case consisting of Velcro, i.e. the anchor 26 is a hooks patch and the inner surface of the end 28 of the sling 22 is a pile patch.

A second adjustable length sling 30, on the outside surface of the inner and outer sides of the upper portion 18 of the shoe 10, extends from proximately the center of the insole 16 external to the upper portion 18 and upwardly and rearwardly from a second adjustable length anchor 32 on the outside surface of the inner side of the upper portion 18 of the shoe 10, to and around the rear 34 of the shoe 10 above the heel 14 to a third adjustable anchor 36 on the outside surface of the outer side of the upper portion 18 of the shoe 10. The anchors 32 and 36 constitute Velcro as was the case with anchor 26.

Thus, the first sling 20 urges the inner side of a right foot inserted into the shoe 10 upwardly and forwardly, and the second sling 30 urges the inner side of the foot upwardly and rearwardly.

Figure 3:
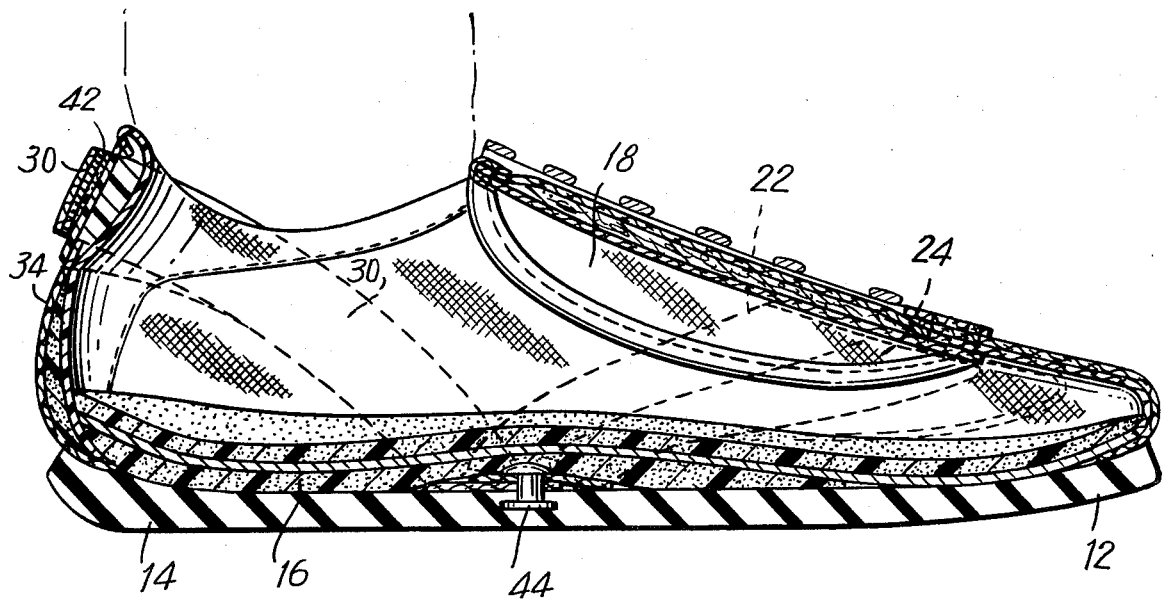
FIG. 3 is a sectional elevation view taken substantially along the line 3—3 of FIG. 1.
Figure 4:
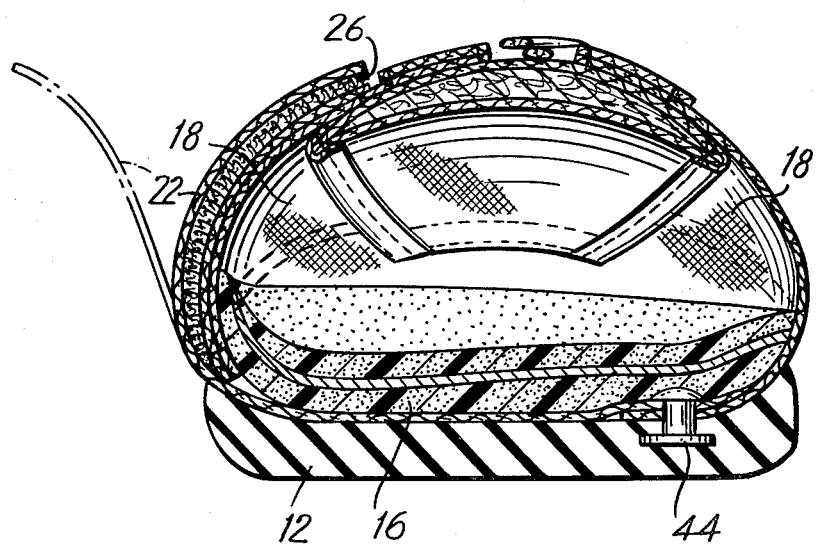
FIG. 4 is a sectional elevation view taken substantially along the line 4—4 of FIG. 1.

FIG. 3 shows another anchor 42 on the rear portion 34 of the shoe 10. FIGS. 3 and 4 show one feasible means of anchoring the inner ends of the slings 20, 30, 38 to the insole 16, namely a rivet 44 proximately at the center of the insole but displaced somewhat towards the outer side of the shoe 10. Other feasible alternates for securing the inner ends of the slings 20 (22, 24), 30 and 38 to the insole 16 include sewing, stitching and stapling.

FIGS. 5, 6 and 6a show an alternative and preferred embodiment of the invention, consisting of an improved shoe with simplified adjustable orthopedic appliance. The shoe 46 in this case is for the right foot and includes a sole portion 48, a heel portion 50, and an upper portion 52. An adjustable length sling 54 is provided on the outside surface of the inner and outer sides of the upper portion 52 of the shoe 46. The sling extends from rivet 56 which is proximately at the center of the insole 58, external to the upper portion 52 and upwardly and rearwardly from a first adjustable anchor 60 on the outside surface of the inner side of the upper portion 52 of the shoe 46, to and around the rear 62 of the upper portion 52 of the shoe 46 above the heel 50, to a second adjustable anchor 64 on the outside surface of the outer side of the upper portion 52 of the shoe 46.

Thus, the sling 54 urges the inner side of the foot upwardly and rearwardly. The shoe 46 and sling 54 also preferably include a third adjustable anchor 66 on the upper portion 52 of the shoe 46. The third anchor 66 is proximately at the rear 62 of the shoe 46 above the heel 50 and on the outside surface of the upper portion 52 of the shoe 46. Thus, the midpoint of the sling 54 is held by the third anchor 66.

The present shoe as exemplified by FIGS. 5 and 6 also preferably includes another adjustable length sling 68 on the outside surface of the inner side of the upper portion 52 of the shoe 46. The sling 68 extends from proximately the center of the insole (rivet 56) external to the upper portion 52 and upwardly to an adjustable anchor 70 on the front part of the upper portion 52 of the shoe 46. The sling 68 urges the inner side of a right foot inserted into the shoe 46 upwardly. Sling 68 penetrates the upper portion 52 to get from the inside of the shoe to the outside of the upper portion.

It thus will be seen that there is provided a shoe with adjustable orthopedic appliance which achieves the various objects of the invention and which is well adapted to meet the conditions of practical use.

As various possible embodiments might be made of the above invention, and as various changes might be made in the embodiments above set forth, it is to be understood that all matter herein described or shown in the accompanying drawings is to be interpreted as illustrative and not in a limiting sense. Thus, it will be understood by those skilled in the art that although preferred and alternative embodiments have been shown and described in accordance with the Patent Statutes, the invention is not limited thereto or thereby.

Having thus described the invention, there is claimed as new and desired to be secured by Letters Patent:

1. A shoe with adjustable orthopedic appliance which comprises a shoe, said shoe having a sole portion, a heel portion, an insole and an upper portion, a first adjustable length sling on the outside surface of the inner side of the upper portion of said shoe, said first sling extending external to said upper portion from approximately the center of said insole, and upwardly to a first adjustable anchor on the front part of said upper portion of said shoe, and a second adjustable length sling on the outside surface of the inner and outer sides of the upper portion of said shoe, said second sling extending from proximately the center of said insole external to said upper portion and upwardly and rearwardly to a second adjustable anchor on the outside surface of the inner side of the upper portion of said shoe, and from said second anchor to and around the rear of the upper portion of said shoe above the heel portion to a third adjustable anchor on the outside surface of the outer side of said upper portion of said shoe, whereby said first sling urges the inner side of a foot inserted into said shoe upwardly, and whereby said second sling urges the inner side of said foot upwardly and rearwardly.

2. The shoe of claim 1 including a fourth adjustable anchor on said upper portion of said shoe, said fourth anchor being proximately at the rear of the shoe above the heel and on the outside surface of the upper portion of the shoe, so that the midpoint of the second sling is held by said fourth anchor.

3. The shoe of claim 1 in which the anchors each comprise a flexible hook patch and a flexible pile patch, one of said patches being secured to a portion of a sling, the other of said patches being secured to the outer surface of the upper portion of the shoe.

4. A shoe with adjustable orthopedic appliance which comprises a shoe, said shoe having a sole portion, a heel portion, an insole and an upper portion, and an adjustable length sling on the outside surface of the inner and outer sides of the upper portion of said shoe, said sling extending from proximately the center of said insole external to said upper portion and upwardly and rearwardly to a first adjustable anchor on the outside surface of the inner side of the upper portion of said shoe, and from said first anchor to and around the rear of the upper portion of said shoe above the heel portion to a second adjustable anchor on the outside surface of the outer side of said upper portion of said shoe, whereby said sling urges the inner side of said foot upwardly and rearwardly, said shoe including a third adjustable anchor on said upper portion of said shoe, said third anchor being proximately at the rear of the shoe above the heel portion and on the outside surface of the upper portion of the shoe, so that the midpoint of said sling is held by said third anchor.

* * * * *